US010896508B2

United States Patent
El Harouni et al.

(10) Patent No.: US 10,896,508 B2
(45) Date of Patent: Jan. 19, 2021

(54) SYSTEM FOR SEGMENTATION OF ANATOMICAL STRUCTURES IN CARDIAC CTA USING FULLY CONVOLUTIONAL NEURAL NETWORKS

(71) Applicant: International Business Machines Corporation, Armonk, NY (US)

(72) Inventors: Ahmed El Harouni, San Jose, CA (US); Mehdi Moradi, San Jose, CA (US); Prasanth Prasanna, San Jose, CA (US); Tanveer F. Syeda-Mahmood, Cupertino, CA (US); Hui Tang, San Jose, CA (US); Gopalkrishna Veni, San Jose, CA (US); Hongzhi Wang, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 223 days.

(21) Appl. No.: 15/963,442

(22) Filed: Apr. 26, 2018

(65) Prior Publication Data
US 2019/0244357 A1    Aug. 8, 2019

Related U.S. Application Data

(60) Provisional application No. 62/627,306, filed on Feb. 7, 2018.

(51) Int. Cl.
*G06T 7/11* (2017.01)
*G06N 3/08* (2006.01)
(Continued)

(52) U.S. Cl.
CPC .................. *G06T 7/11* (2017.01); *G06K 9/66* (2013.01); *G06N 3/08* (2013.01); *G06T 7/0012* (2013.01);
(Continued)

(58) Field of Classification Search
CPC .. G06K 9/66; G06N 3/08; G06T 2207/10072; G06T 2207/10081; G06T 2207/20081;
(Continued)

(56) References Cited

U.S. PATENT DOCUMENTS

| 5,903,664 A | 5/1999 | Hartley et al. |
| 7,809,190 B2 | 10/2010 | Rousson et al. |

(Continued)

FOREIGN PATENT DOCUMENTS

| CN | 106897993 A | 6/2017 |
| CN | 107203989 A | 9/2017 |
| WO | WO2017/091833 A1 | 6/2017 |

OTHER PUBLICATIONS

Zreik, Majd, et al. "Deep learning analysis of the myocardium in coronary CT angiography for identification of patients with functionally significant coronary artery stenosis." Medical image analysis 44 (2018): 72-85. (Year: 2017).*

(Continued)

*Primary Examiner* — Nirav G Patel
(74) *Attorney, Agent, or Firm* — Stephen R. Tkacs; Stephen J. Walder, Jr.; William J. Stock

(57) ABSTRACT

A method comprises (a) collecting (i) a set of chest computed tomography angiography (CTA) images scanned in the axial view and (ii) a manual segmentation of the images, for each one of multiple organs; (b) preprocessing the images such that they share the same field of view (FOV); (c) using both the images and their manual segmentation to train a supervised deep learning segmentation network, wherein loss is determined from a multi-dice score that is the summation of the dice scores for all the multiple organs, each dice score being computed as the similarity between the manual segmentation and the output of the network for one of the organs; (d) testing a given (input) pre-processed (Continued)

image on the trained network, thereby obtaining segmented output of the given image; and (e) smoothing the segmented output of the given image.

17 Claims, 10 Drawing Sheets

(51) Int. Cl.
*G16H 30/20* (2018.01)
*G06T 7/00* (2017.01)
*G06T 7/194* (2017.01)
*G06K 9/66* (2006.01)

(52) U.S. Cl.
CPC .............. *G06T 7/194* (2017.01); *G16H 30/20* (2018.01); *G06T 2207/10072* (2013.01); *G06T 2207/10081* (2013.01); *G06T 2207/20081* (2013.01); *G06T 2207/30048* (2013.01); *G06T 2207/30101* (2013.01)

(58) Field of Classification Search
CPC . G06T 2207/30048; G06T 2207/30101; G06T 7/0012; G06T 7/11; G06T 7/194; G16H 30/20; G16H 30/40; G16H 50/70
See application file for complete search history.

(56) References Cited

U.S. PATENT DOCUMENTS

| | | | |
|---|---|---|---|
| 7,916,919 | B2 | 3/2011 | Zheng et al. |
| 8,494,236 | B2 | 7/2013 | Jolly et al. |
| 9,262,834 | B2 | 2/2016 | Molnar et al. |
| 9,824,456 | B2 | 11/2017 | Noga et al. |
| 2017/0109881 | A1 | 4/2017 | Avendi et al. |
| 2017/0231713 | A1 | 8/2017 | Siewerdsen |
| 2019/0080456 | A1* | 3/2019 | Song .................. G06N 3/00 |
| 2019/0147589 | A1* | 5/2019 | Zhou .................. G06T 7/0012 382/131 |

OTHER PUBLICATIONS

Dou, Qi, et al. "3D deeply supervised network for automated segmentation of volumetric medical images." Medical image analysis 41 (2017): 40-54. (Year: 2017).*

International Search Report and Written Opinion dated May 13, 2019 for International Application No. PCT/IB2019/050377, 9 pages.

Ehara, Mariko et al., "Diagnostic Accuracy of 64-Slice Computed Tomography for Detecting Angiographically Significant Caronary Artery Stenosis in an Unselected Consecutive Patient Papulation", Circulation Journal, vol. 70, May 2006, 8 pages.

Giannakidis, Archontis et al., "Fast Fully Automatic Segmentation of the Severely Abnormal Human Right Ventricle from Cardiovascular Magnetic Resonance Images using a Multi-scale 3D Convolutional Neural Network", IEEE, 2016 12th International Conference on Signal-Image Technology & Internet-Based Systems, Nov. 28, 2016, pp. 42-46.

Kirisli, H. A. et al., "Evaluation of a multi-atlas based method for segmentation of cardiac CTA data: a large scale, multicenter, and multivendor study", American Association of Physicists in Medicine, Medical Physics, vol. 37, No. 12, Dec. 10, pp. 6279-6291.

Milletari, Fausto et al., "V-Net: Fully Convolutional Neural Networks for Volumetric Medical Image Segmentation", GitHub, Inc., http://carnpar.in.turn.de/pub/milletari2016Vnet/milletari2016Vnet.pdf, VITAL Literature Review, Jun. 15, 2016, 11 pages.

Mitchell, Steven C. et al., "3-D Active Appearance Models: Segmentation of Cardiac MR and Ultrasound Images", IEEE, IEEE Transactions on Medical Imaging, vol. 21, No. 9, Sep. 2002, pp. 1167-1178.

Moeskops, Pim et al., "Deep Learning for Multi-Task Medical Image Segmentation in Multiple Modalities", Springer International Publishing, International Conference on Medical Image Computing and Computer-Assisted Intervention, Oct. 17, 2016, pp. 478-486.

Roth, Holger R. et al., "Deep convolutional networks for pancreas segmentation in CT imaging", SPIE Medical Imaging 2015, Feb. 21-26, 2015, Orlando, FL, 8 pages.

Tang, Hui et al., "Segmentation of anatomical structures in cardiac CTA using multi-label V-Net", SPIE, Proceedings of SPIE Medical Imaging 2018: Image Processing, vol. 10574, Houston, Texas, Mar. 2, 2018, 5 pages.

Wang, Hongzhi et al., "Fast Anaiomy Segmamizztion by Combiming Low Resoiutim Multi-Atlas Label Fusion with High Resolution Corrective Learning: An Experimentai Study,", 2017 IEEE 14th International Symposium on Biomedical Imaging (ISBI 2017), Apr. 18-21, 2017, 4 pages.

Zheng, Yefeng et al., "Fast Automatic Heart Chamber Segmentation from 3D CT Data Using Marginal Space Learning and Steerable Features", ICCV 2007, Eleventh IEEE International Conference on Computer Vision, Rio de Janeiro, Brazil, Oct. 14-20, 2007, 8 pages.

Zuluaga, Maria A. et al., "Multi-atlas Propagation Whole Heart Segmentation from MRI and CTA Using a Local Normalised Correlation Coefficient Criterion", Springer, Berlin, Heidelberg, International Conference on Functional Imaging and Modeling of the Heart, Jun. 20, 2013, pp. 174-181.

Hu, Peijun et al., "Automatic abdominal multi-organ segmentation using deep convolutional neural network and time-implicit level sets", Int J CARS 12, (2017), Published Nov. 24, 2016, https://doi.org/10.1007/s11548-016-1501-5 (Abstract Only), 2 pages.

Shahzad, Rahil et al., "Automatic Segmentation and Quantification of the Cardiac Structures from Non-contrast-enhanced Cardiac CT Scans", Published Apr. 11, 2017, 2017 Institute of Physics and Engineering in Medicine Physics in Medicine & Biology, vol. 62, No. 9, 18 pages.

* cited by examiner

SYSTEM FOR SEGMENTATION OF ANATOMICAL STRUCTURES IN CARDIAC CTA USING FULLY CONVOLUTIONAL NEURAL NETWORKS

BACKGROUND

The present application relates generally to an improved data processing apparatus and method and more specifically to mechanisms for segmentation of anatomical structures in cardiac CTA using fully convolutional neural networks.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method comprises (a) collecting (i) a set of chest computed tomography angiography (CTA) images scanned in the axial view and (ii) a manual segmentation of the images, for each one of multiple organs; (b) preprocessing the images such that they share the same field of view (FOV); (c) using both the images and their manual segmentation to train a supervised deep learning segmentation network, wherein loss is determined from a multi-dice score that is the summation of the dice scores for all the multiple organs, each dice score being computed as the similarity between the manual segmentation and the output of the network for one of the organs; (d) testing a given (input) pre-processed image on the trained network, thereby obtaining segmented output of the given image; and (e) smoothing the segmented output of the given image.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
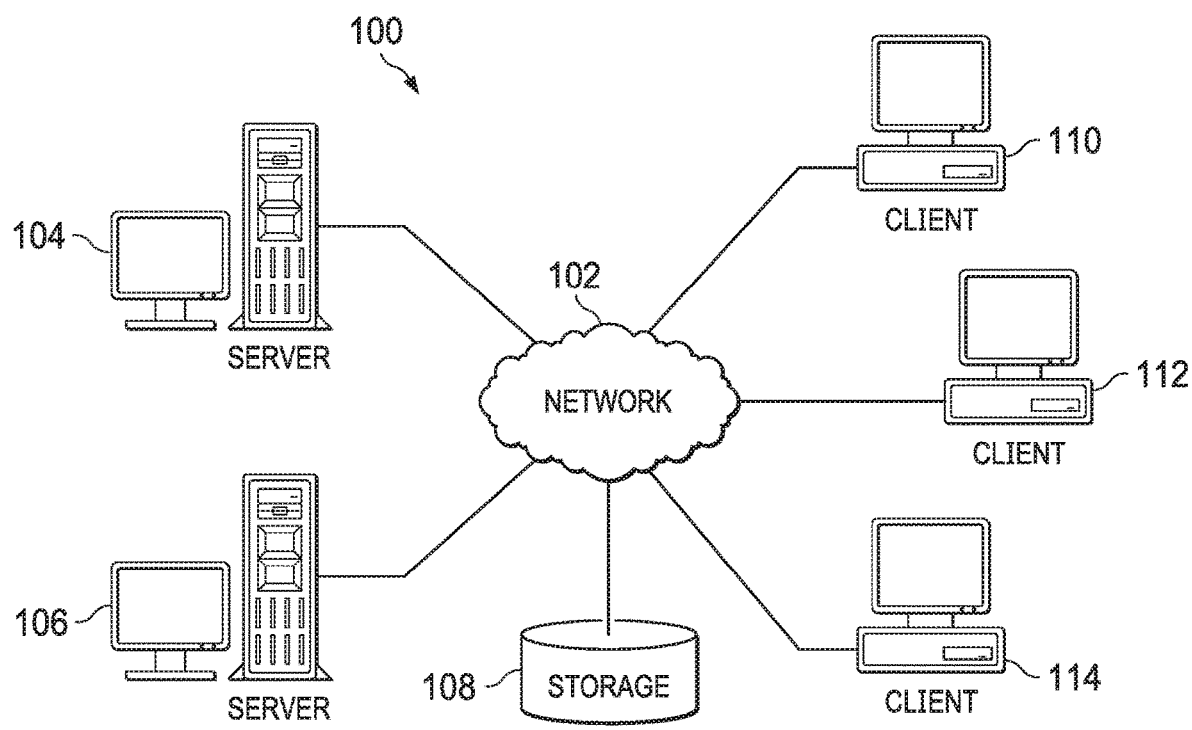
FIG. 1 is an example diagram of a distributed data processing system in which aspects of the illustrative embodiments may be implemented.

Segmenting anatomical structures in the chest, such as the heart chambers, different segments of the pulmonary and different segments of the aorta is a crucial step in many automatic disease detection applications. Multiatlas based methods are developed for this task and achieve stable and excellent results. However, due to the required deformable registration step, they are often computationally expensive and create a bottle neck in terms of processing time. In contrast, convolutional neural networks (CNNs) with 2D or 3D kernels, although slow to train, are very fast in the deployment stage and have been employed to solve segmentation tasks in medical imaging. A recent improvement in performance of neural networks in medical image segmentation was reported when dice similarity coefficient (DSC) was used to optimize the weights in a fully convolutional architecture called V-Net. However, in the previous work, only the DSC calculated for one foreground object is optimized, as a result the DSC based segmentation CNNs are only able to perform a binary segmentation. In this paper, we extend the V-Net binary architecture to a multi-label segmentation network and use it for segmenting multiple anatomical structures in cardiac CTA. The method uses multi-label V-Net optimized by the sum over DSC for all the anatomies, followed by a post-processing method to refine the segmentation surface. Our method takes averagely less than 10 sec to segment a full CTA volume. Our method achieves an average DSC of 77% for 16 segmented anatomies using four-fold cross validation.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

Other definitions, explicit and implicit, may be included below:

Atlas: A CTA image and the manual segmentation mask for a collection of anatomies.

Multi-atlas: Multiple CTA images and their manual segmentation mask for a collection of anatomies.

Neural network: Artificial neural networks (ANNs) or connectionist systems are computing systems vaguely inspired by the biological neural networks that constitute animal brains. Such systems "learn" (i.e., progressively improve performance on) tasks by considering examples, generally without task-specific programming.

Convolutional neural network: A convolutional neural network (CNN) is a class of deep, feed-forward networks, composed of one or more convolutional layers with fully connected layers (matching those in typical ANNs) on top. A CNN uses tied weights and pooling layers. This architecture allows CNNs to take advantage of the 2D structure of input data.

Dice: A measure that judges whether segmentation is good or not good. A dice score is generally between 0 and 1, wherein a higher dice score indicates a good segmentation.

Dice similarity coefficient (DSC): A coefficient used as a statistical validation metric to evaluate the performance of both the reproducibility of manual segmentations and the spatial overlap accuracy of automated probabilistic fractional segmentation of MR images, illustrated on two clinical examples.

Loss: A measure calculated on training and testing indicating how well the model is doing for these two sets. The lower the loss, the better.

Computed tomography angiography (CTA): Computed tomography angiography (also called CT angiography or CTA) is a computed tomography technique used to visualize arterial and venous vessels throughout the body. This ranges from arteries serving the brain to those bringing blood to the lungs, kidneys, arms and legs.

V-Net: Fully convolutional neural networks for volumetric medical image segmentation.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
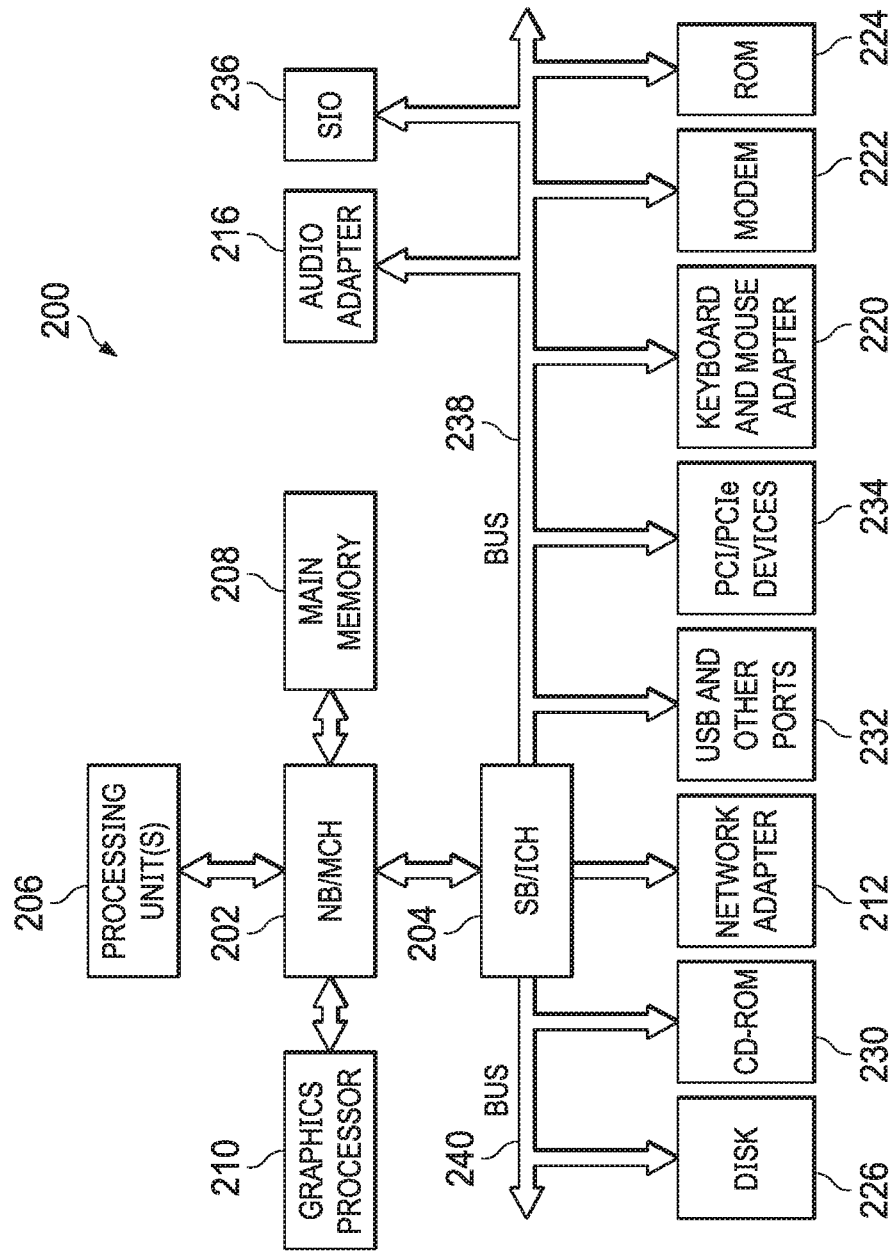
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104, may be specifically configured to implement segmentation of anatomical structures in cardiac CTA using fully convolutional neural networks. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates segmentation of anatomical structures in cardiac CTA using fully convolutional neural networks.

As noted above, the mechanisms of the illustrative embodiments utilize specifically configured computing devices, or data processing systems, to perform the operations for segmentation of anatomical structures in cardiac CTA using fully convolutional neural networks. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external effects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System p® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the segmentation of anatomical structures in cardiac CTA using fully convolutional neural networks.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Contrast enhanced chest computerized tomography (CT) is able to assess the ventricular and atrial functions and show many disorders of the heart, lungs, or main arteries in the chest, including: pulmonary embolism, suspected blockage of the superior vena cava, abnormalities of the blood vessels such as coronary artery atherosclerosis, aortic aneurysm and aortic dissection. Several biomarkers such as myocardial mass and volume of heart chambers are needed to be quantified for assessing the ventricular and atrial functions. Furthermore, localization of the main arteries in the chest is also used as a pre-processing step in many disease detection algorithms. Segmentation of the anatomical structures is a crucial for the biomarker quantification and disease detection.

Many approaches such as active appearance model, multi-atlas registration and marginal space learning are proposed for the heart anatomies and great vessels segmentation. Multi-atlas segmentation is widely used for the segmentation of heart chambers and for the segmentation of whole chest anatomies because of its high robustness and outstanding performance. The multi-atlas segmentation algorithm includes a deformable registration step that aligns multiple atlases to a target image, and a label fusion step to resolve conflicting labels produced by multiple atlases. However, due to the heavy computation in the registration and voxel-wise label fusion step, the multi-atlas based methods are very time consuming. As a result, researchers have reported work on reducing the computational cost involved in these approaches. One prior art approach performed an atlas selection method prior to the registration step to achieve better segmentation accuracy and reduce computational cost. Another prior art approach used non-local label fusion techniques for brain tissue segmentation. Yet another prior art approach did an experimental study to investigate the role of corrective learning in speeding up multi-atlas learning. They first perform the multi-atlas segmentation in a low resolution space and up-sample back to the original high resolution space. The resulting segmentation errors are corrected using supervised learning. The method reduces the time cost dramatically while preserving segmentation accuracy close to the result obtained directly from the high resolution space.

CNNs have shown promising results in medial image segmentation for both two-dimensional (2D) tasks and three-dimensional (3D) tasks. Fully convolutional networks (FCN) have been proposed for natural red-green-blue (RGB) image segmentation and further used for cardiac segmentation in Short-Axis medical resonance imaging (MRI). Another prior art approach proposed the U-Net network and applied it to transmitted light microscopy images. To incorporate context from the neighboring slices, the M-Net architecture proposed flattens several slices into one slice and feeds into a 2D CNN segmentation network. The M-Net was applied for brain tissue segmentation in MRI. Another prior art approach extended the U-Net by replacing all the 2D components with 3D.

One particular prior art approach proposed V-Net structure for 3D volume segmentation. One of the main contributions in V-Net is that DSC is computed and optimized in the loss layer, and is propagated back to optimize the network weights. V-Net is tested on prostate segmentation in MRI. However, the original V-Net is developed for binary segmentation tasks. In case of applying on multi-label segmentation tasks, a new DSC based loss layer should be developed.

The illustrative embodiment extends the binary V-Net into a multi-label segmentation network. The illustrative embodiment uses the sum of DSC calculated for all the anatomical structures of interest in the loss layer. The segmentation result from multi-label V-Net is then smoothed to remove minor segmentation errors and refine the object surface.

The illustrative embodiment collects 48 cardiac CTA volumes annotated for 16 anatomical structures by one radiologist. The 16 anatomies are: sternum, ascending/descending/arch/root aorta, left/right/trunk pulmonary artery, vertebrae, left/right atrium, left/right ventricle, left ventricular myocardium, and superior/inferior vena cava similar to. The cardiac CT studies used in our study were acquired by a CT scanner. Each image has isotropic in-plane resolutions under 1 mm*1 mm. The slice thickness varies from 0.8 mm to 2.0 mm. All the images are intensity equalized to eliminate the intensity variation between patients and then resampled to voxel size of 1.5 mm in all dimensions.

There are three aspects that make V-Net a powerful deep network for volume image segmentation. First, it uses volumetric kernels in each convolutional layer. Second, it learns a residual function at each stage of different resolutions. Third, it optimizes the DSC of the foreground object to avoid unbalancing between the background and the foreground volume. One prior art approach reported improved segmentation results compared to the same architecture trained by optimizing a multi-nominal logistic loss with sample re-weighting. However, in the prior work, only the DSC of single foreground is optimized.

To extend V-Net to a multi-label network, consider a segmentation problem where the goal is to find segmentation mask image $F_i$, for anatomical structure i, by establishing that $f_j^i \in F_i$, where $f_j^i$ is the $j^{th}$ voxel of the $i^{th}$ segmented foreground, given the ground truth that $g_j^i$ is in the $i^{th}$ ground truth structure, 1<i<16 in our application. The overall DSC between the segmentation and the ground truth can be differentiated w.r.t the $i^{th}$ segmentation's $j^{th}$ voxel, yielding the gradient:

$$\frac{\delta D}{\delta f_j^i} = 2\left(\frac{g_j^i\left(\sum_n^N f_n^{i2} + \sum_n^N g_n^{i2}\right) - 2f_j^i \sum_n^N f_n^i g_n^i}{\left(\sum_n^N f_n^{i2} + \sum_n^N g_n^{i2}\right)^2}\right)$$

where N is the total number of voxels in the image. Due to the high memory requirements in 3D convolution, the input image is downsampled to 2 mm*2 mm*3.5 mm, and a subimage of size 128*192*64 is cropped from the center of the original image and fed to the network. At testing time, the output of the multi-label V-Net is up-sampled to the original resolution and padded to the original image size for evaluation.

Since the input is down-sampled, the segmentation result from multi-label V-Net is coarse after up-sampling back to the original resolution. Additionally, V-Net does not incorporate any shape prior information. As a result the outcome usually needs smoothing. For the first issue, future upgrade in hardware can help. For the second issue, one prior art approach proposed to train an auto-encoder and use the mean absolute difference between encoded segmentation and ground truth as the loss. However, extending this approach to a loss function that is calculated based on DSC is not straightforward.

The illustrative embodiment proposes to smooth the segmentation surface by evolving the surface using surface curvature as the evolving speed of the front contour. Some of the abrupt discontinuities in the segmentation disappear due to the fact they cause high curvature in the surface. As the final step of smoothing, the illustrative embodiment extracts the largest independent component for each foreground.

Figure 3:
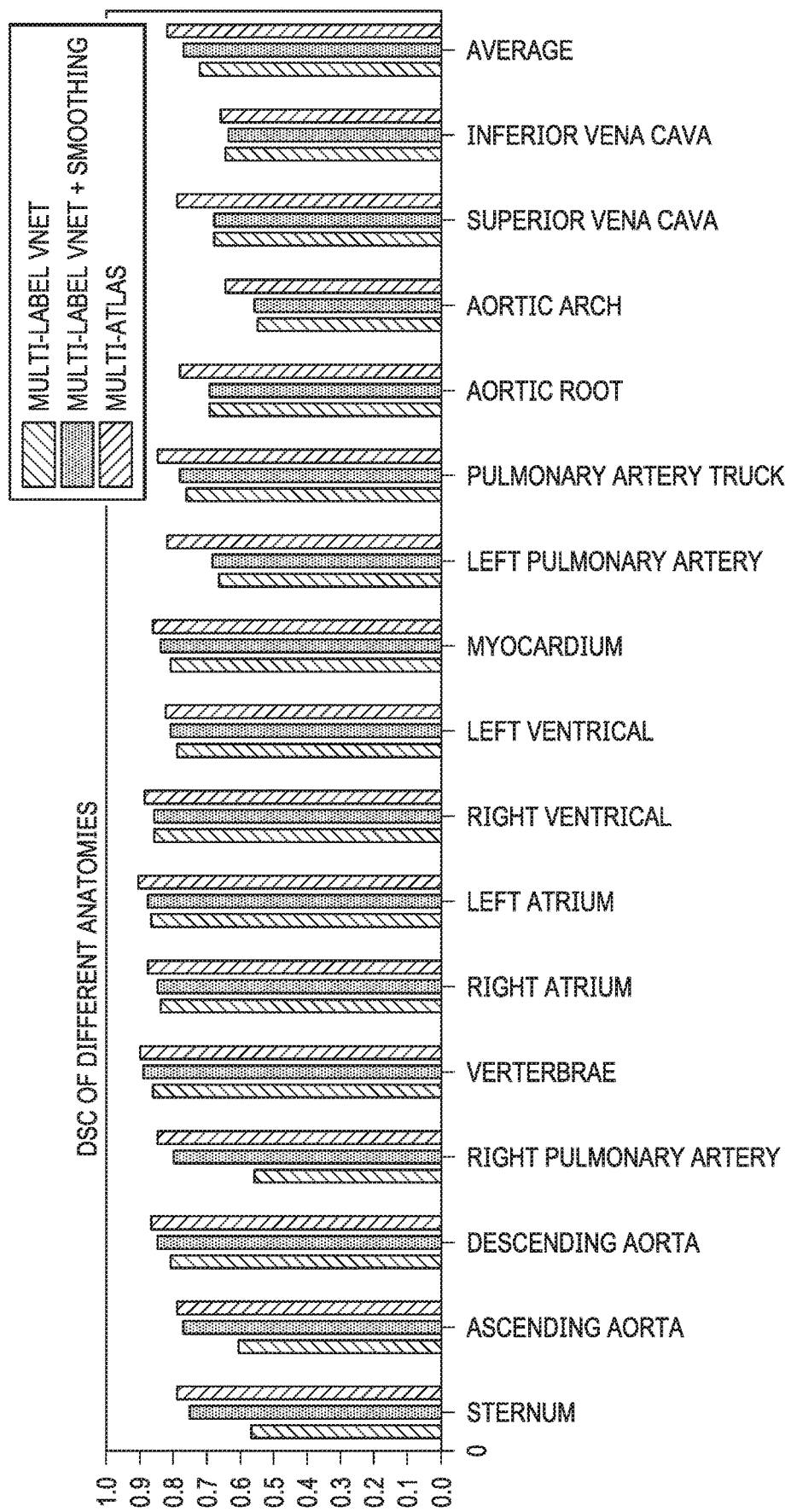
FIG. 3 is a bar plot of the DSC of each anatomy and the average DSC for different methods.

FIG. 3 is a bar plot of the DSC of each anatomy and the average DSC for different methods. FIG. 4 is a 2D visualization of the segmentation, a: original image, b: result from multi-label V-Net, b: result after post-processing, d: ground truth. FIG. 5 is a 3D volume rendering of the segmentation, a: result from multi-label V-Net, b: result after post-processing, c: ground truth.

The illustrative embodiment evaluates the proposed multi-label V-Net network using four-fold cross validation. The average DSC values for different anatomies are shown in FIG. 3. Before smoothing, the average DSC is 0.72 compared to 0.77 after smoothing. As seen in FIG. 3, for 15 of the 16 anatomies, the DSC was improved after smoothing.

Figure 4A:
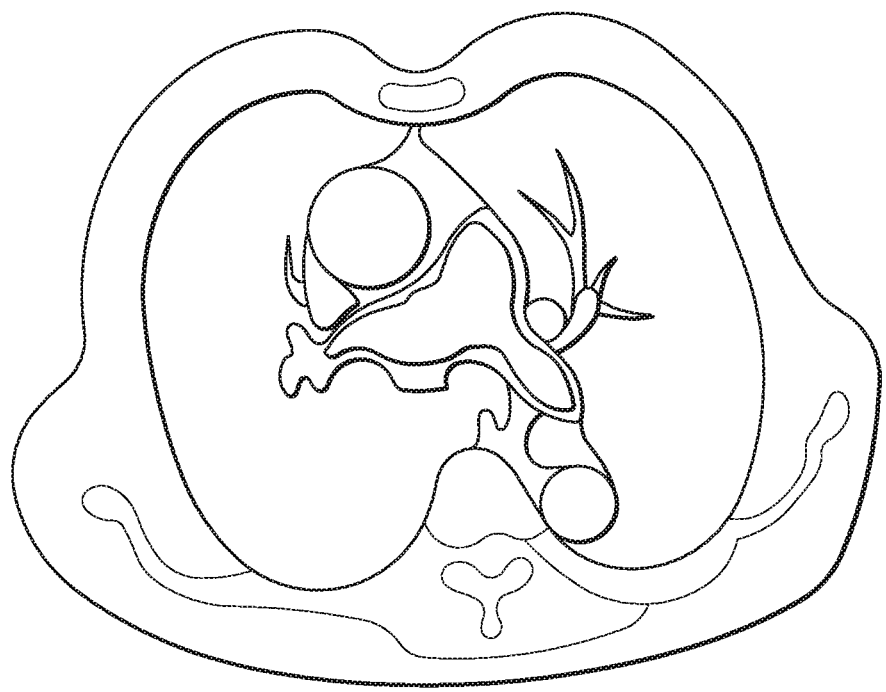
FIG. 4A is a 2D visualization of the segmentation of an original image in accordance with an illustrative embodiment.
Figure 4B:
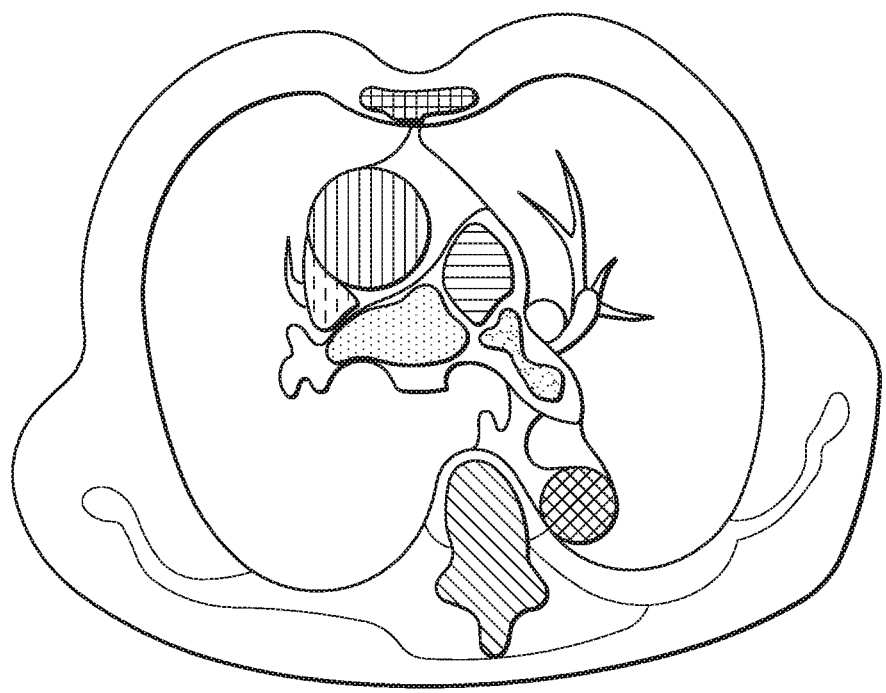
FIG. 4B is a 2D visualization of the segmentation of result from multi-label V-Net in accordance with the illustrative embodiment.
Figure 4C:
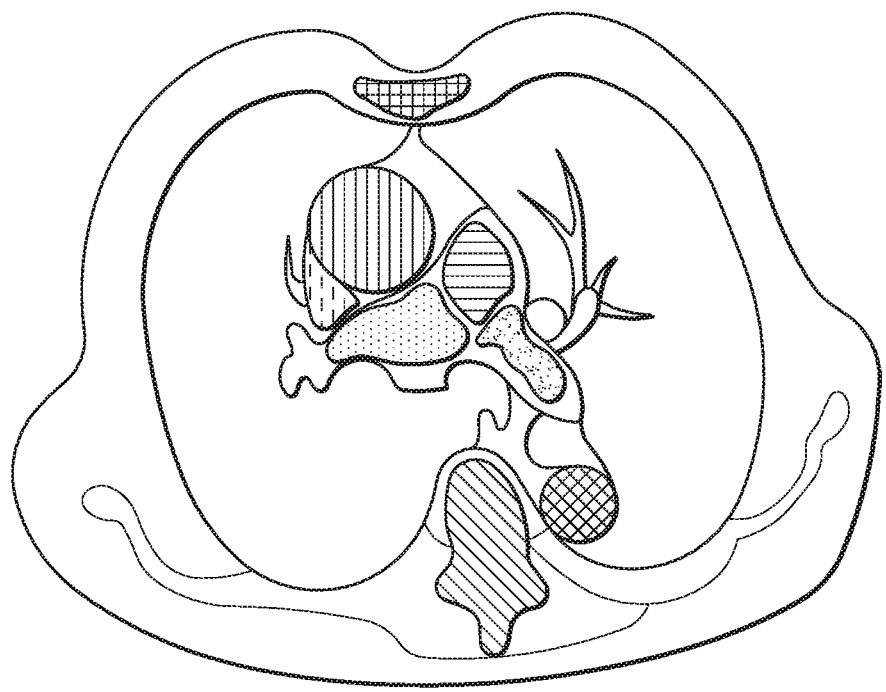
FIG. 4C is a 2D visualization of the segmentation of a result after post-processing in accordance with an illustrative embodiment.
Figure 4D:
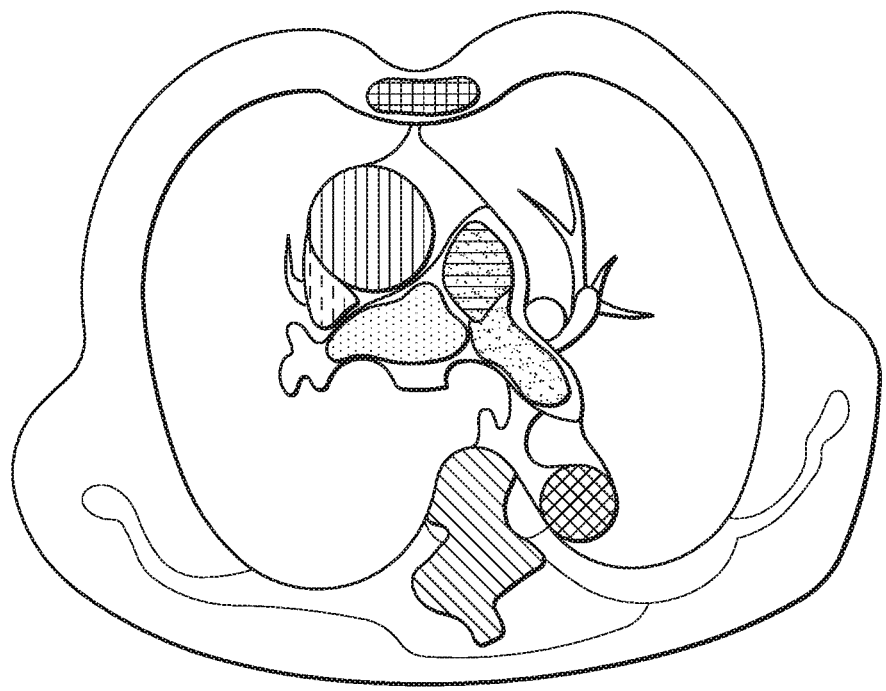
FIG. 4D is a 2D visualization of the segmentation of the ground truth in accordance with the illustrative embodiment.

FIG. 4A is a 2D visualization of the segmentation of an original image in accordance with an illustrative embodiment. FIG. 4B is a 2D visualization of the segmentation of result from multi-label V-Net in accordance with the illustrative embodiment. FIG. 4C is a 2D visualization of the segmentation of a result after post-processing in accordance with an illustrative embodiment. FIG. 4D is a 2D visualization of the segmentation of the ground truth in accordance with the illustrative embodiment.

Figure 5A:
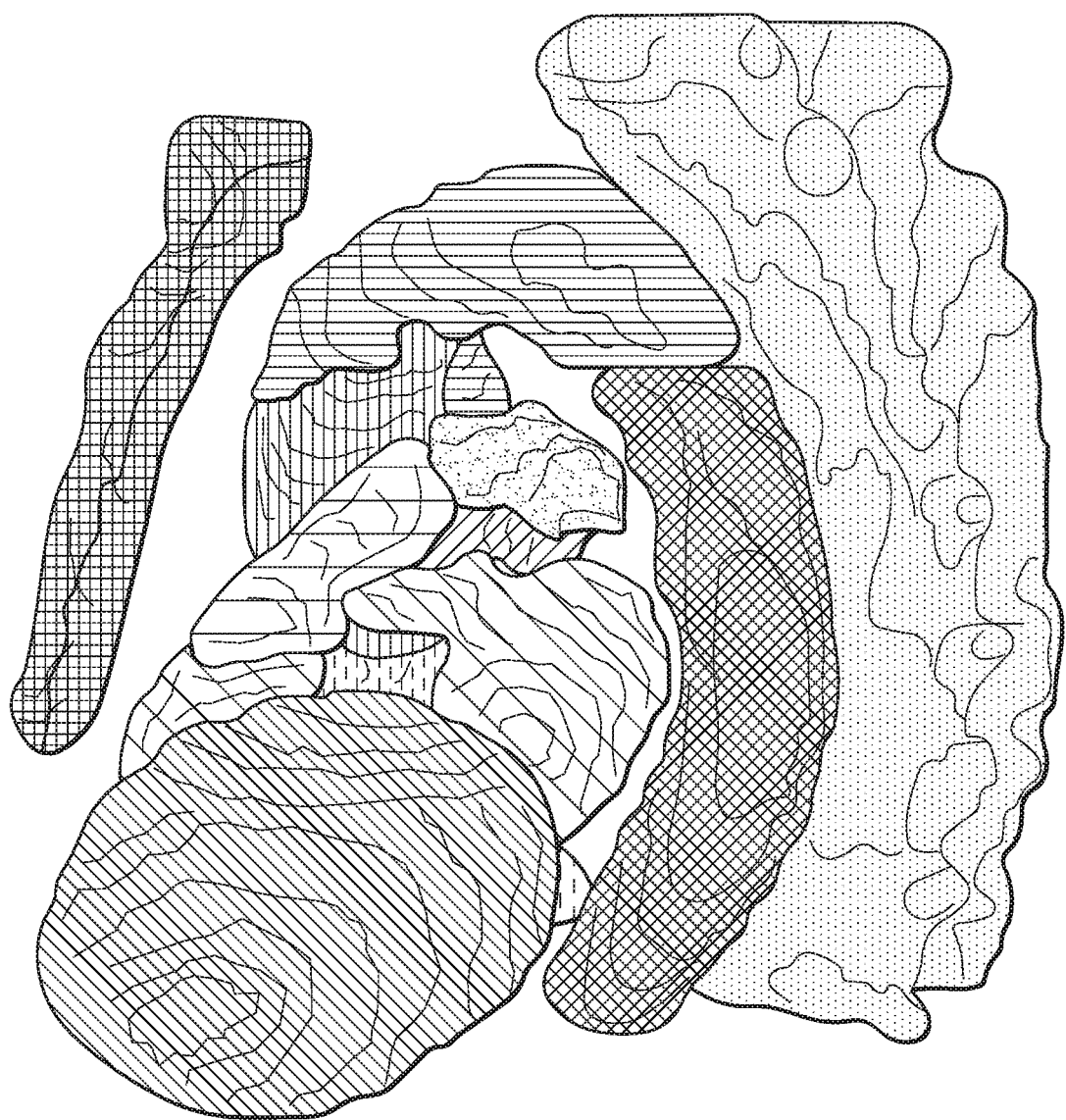
FIG. 5A is a 3D volume rendering of the segmentation of a result from multi-label V-Net in accordance with an illustrative embodiment.
Figure 5B:
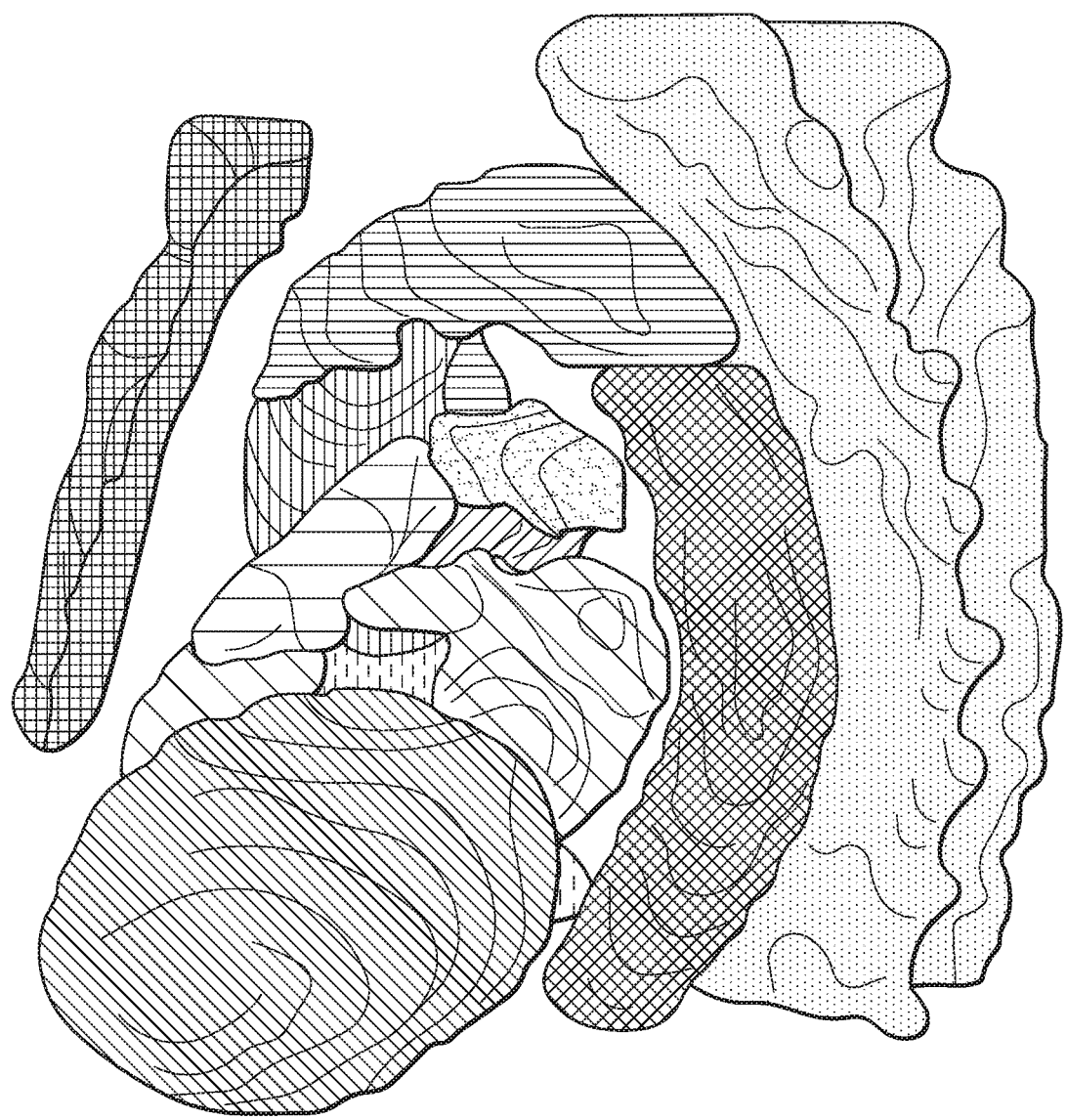
FIG. 5B is a 3D volume rendering of the segmentation of a result after post-processing in accordance with an illustrative embodiment.
Figure 5C:
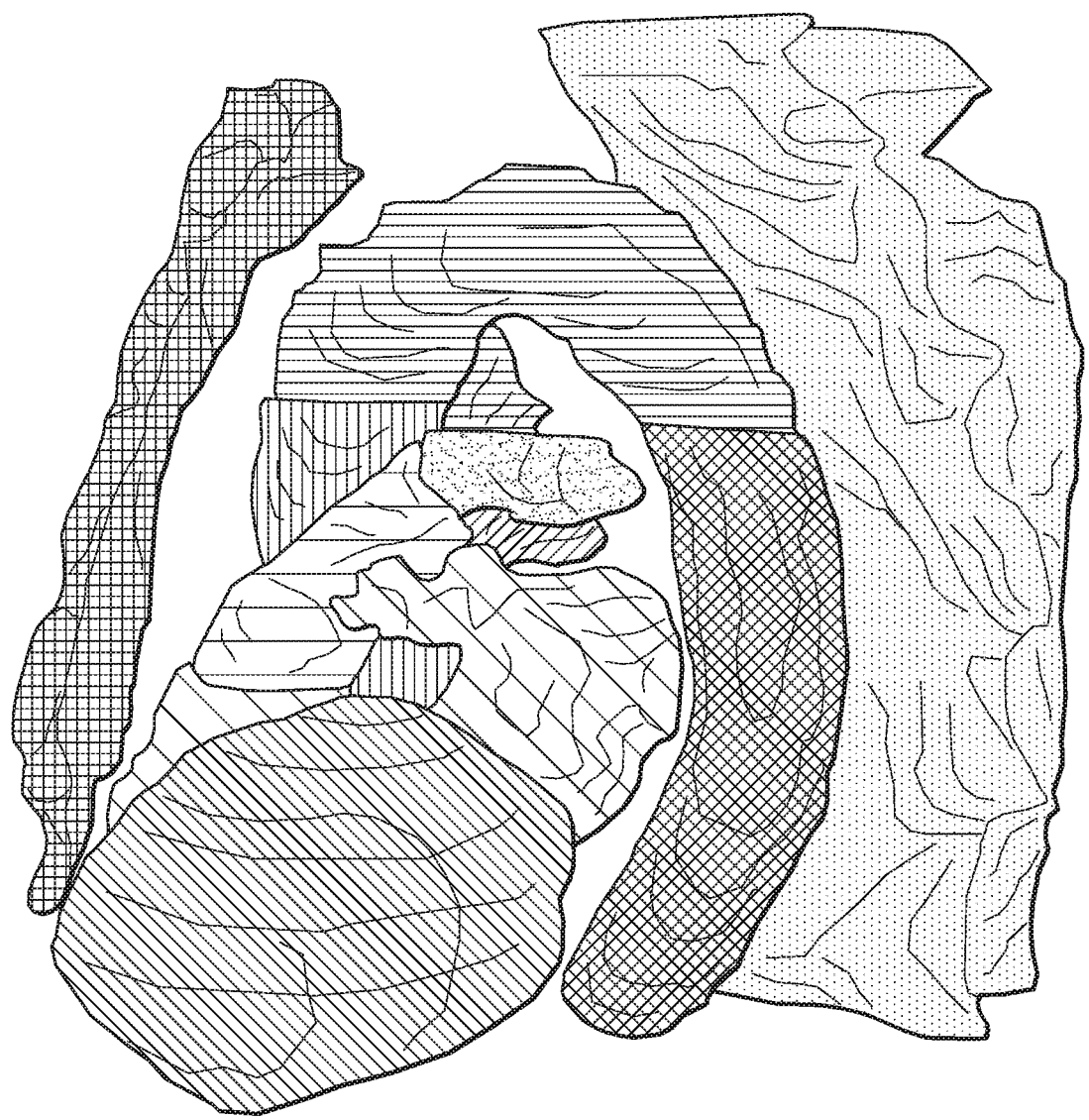
FIG. 5C is a 3D volume rendering of the segmentation of the ground truth in accordance with an illustrative embodiment.

FIG. 5A is a 3D volume rendering of the segmentation of a result from multi-label V-Net in accordance with an illustrative embodiment. FIG. 5B is a 3D volume rendering of the segmentation of a result after post-processing in accordance with an illustrative embodiment. FIG. 5C is a 3D volume rendering of the segmentation of the ground truth in accordance with an illustrative embodiment.

The illustrative embodiment compares the segmentation results to the multi-atlas registration and labels fusion method published, which is the fastest so far. The results of that publication show an average overall DSC of 0.78; however, this was achieved on a subset of the 48 datasets. For a fair comparison, the illustrative embodiment repeated the experiment on the expanded set. Averaged over all structures, the illustrative embodiment achieves DSC of 0.77 compared to 0.82 on the same data for the prior art multi-atlas method. It should be noted that direct comparison is still challenging since the illustrative embodiment down sampled the images to size of 2 mm*2 mm*3.5 mm, but the atlases were at re-sampled voxel size of 1.5 mm*1.5 mm*6 mm.

The main advantage of the illustrative embodiment is in reducing the time cost at the testing/deployment stage, particularly when performed on a graphics processing unit (GPU). It takes less than 10 seconds for the multi-label V-Net to segment a 3D volume on one TITAN X GPU with 12 GB of memory, while it takes around 10 minutes for the multi-atlas segmentation method on Intel® Xeon® CPU E5-2620 v2 with frequency of 2.10 GHz. This was achieved after parallelizing the registration of different atlases.

An advantage of the multi-atlas label fusion method is in more accurate segmentation of small anatomical structures. In the application of the illustrative embodiment this is evident in case of the left pulmonary artery, superior vena cava and aortic arch, which is missing in most cases. As FIG. 3 shows, the multi-atlas label fusion method returns DSC of 0.82, where the smoothed V-Net results in DSC of 0.68, for the left pulmonary artery.

The illustrative embodiment proposes a multi-label V-Net objective function based on the overall DSC of different foregrounds to segment the main anatomical structures in chest CTA. This method was trained and evaluated using four-fold cross validation and achieves results close to the state-of-the-art multi-atlas segmentation method for big anatomies. The method is very efficient at deployment time.

Figure 6:
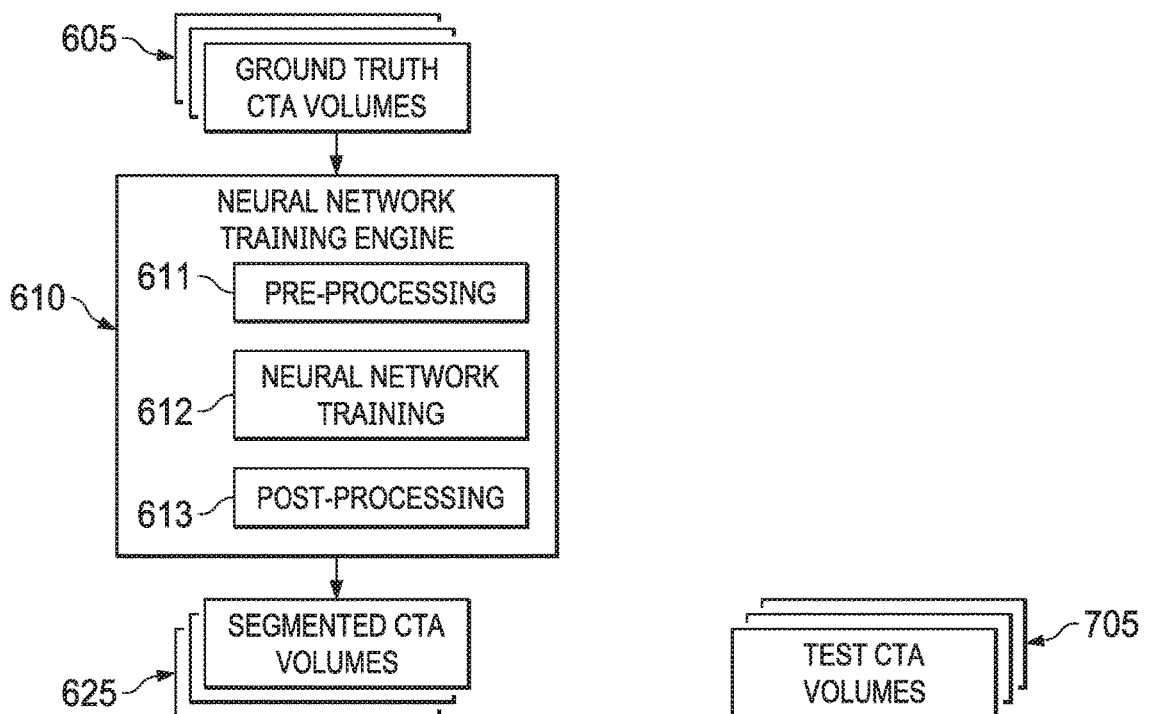
FIG. 6 is a block diagram illustrating a neural network training engine for segmentation of anatomical structures in cardiac CTA using multi-label V-Net in accordance with an illustrative embodiment.

FIG. 6 is a block diagram illustrating a neural network training engine for segmentation of anatomical structures in cardiac CTA using multi-label V-Net in accordance with an illustrative embodiment. Neural network training engine 610 receives a plurality of ground truth CTA volumes 605. These CTA volumes 605 are training instances that are annotated for multiple anatomical structures by one or more radiologists. The multiple anatomical structures may include: ascending/descending/arch/root aorta, left/right/trunk pulmonary artery, vertebrae, left/right atrium, left/right ventricle, left ventricular myocardium, and/or superior/inferior vena cava, for example.

Neural network training engine 610 includes pre-processing component 611, neural network training component 612, and post-processing component 613. Pre-processing component 611 performs one or more pre-processing operations on ground truth CTA volumes 605. In one embodiment, the pre-processing operations may include down-sampling and cropping images in the CTA volumes 605. More particularly, the pre-processing operations may comprise intensity equalizing the images to eliminate the intensity variation between patients and then resampling to a larger voxel size.

Neural network training component 612 uses ground truth CTA volumes 605 to train a neural network to generate segmented CTA volumes 625. In accordance with the illustrative embodiment, the neural network may be a V-Net neural network that is extended to a multi-label network to consider a segmentation problem where the goal is to find segmentation mask images for multiple anatomical structures. Thus, the neural network is trained to identify multiple anatomical structures, such as organs, simultaneously. Neural network training component 612 trains the neural network by using images and manual segmentation to train a supervised deep learning segmentation network, wherein the loss is determined from a multi-dice score that is a summation of the dice scores for the multiple anatomical structures.

Post-processing component 613 performs at least one post-processing operation on the results of segmentation component 612. In one embodiment, the post-processing operations include up-sampling and smoothing the results of segmentation component 612. More particularly, the post-processing operations may comprise smoothing the segmentation surface by evolving the surface using surface curvature as the evolving speed of the front contour.

Figure 7:
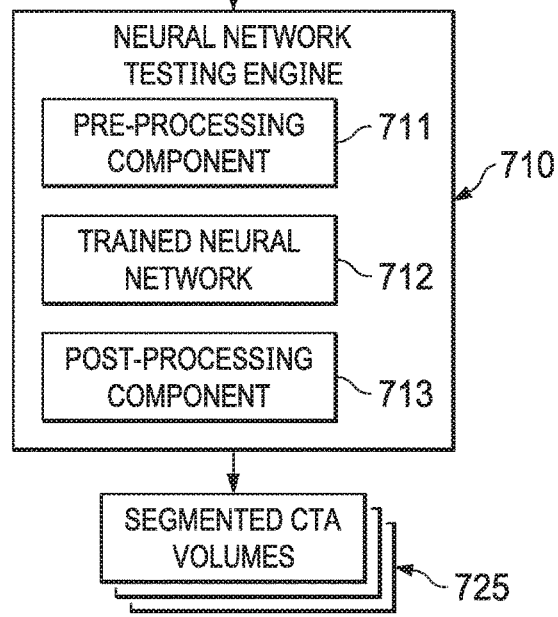
FIG. 7 is a block diagram of a neural network testing engine for segmentation of anatomical structures in cardiac CTA using multi-label V-Net in accordance with an illustrative embodiment.

FIG. 7 is a block diagram of a neural network testing engine for segmentation of anatomical structures in cardiac CTA using multi-label V-Net in accordance with an illustrative embodiment. Neural network testing engine 710 receives a plurality of test CTA volumes 705. These CTA volumes 705 are test instances that may be annotated for multiple anatomical structures by one or more radiologists. The multiple anatomical structures may include: ascending/descending/arch/root aorta, left/right/trunk pulmonary artery, vertebrae, left/right atrium, left/right ventricle, left ventricular myocardium, and/or superior/inferior vena cava, for example.

Neural network testing engine 710 includes pre-processing component 711, trained neural network 712, and post-processing component 713. Pre-processing component 711 performs one or more pre-processing operations on ground truth CTA volumes 705. In one embodiment, the pre-processing operations may include down-sampling and cropping images in the CTA volumes 705. More particularly, the pre-processing operations may comprise intensity equalizing the images to eliminate the intensity variation between patients and then resampling to a larger voxel size.

Trained neural network 712 operates to segment test CTA volumes 705 to generate segmented CTA volumes 725. In accordance with the illustrative embodiment, the trained neural network 712 may be a V-Net neural network that is extended to a multi-label network to consider a segmentation problem where the goal is to find segmentation mask images for multiple anatomical structures. The neural network 712 is trained to identify multiple anatomical structures, such as organs, simultaneously. Neural network 712 is a supervised deep learning segmentation network, wherein the loss is determined from a multi-dice score that is a summation of the dice scores for the multiple anatomical structures.

Post-processing component 713 performs at least one post-processing operation on the results of the trained neural network 712. In one embodiment, the post-processing operations include up-sampling and smoothing the results of trained neural network 712. More particularly, the post-processing operations may comprise smoothing the segmentation surface by evolving the surface using surface curvature as the evolving speed of the front contour.

Figure 8:
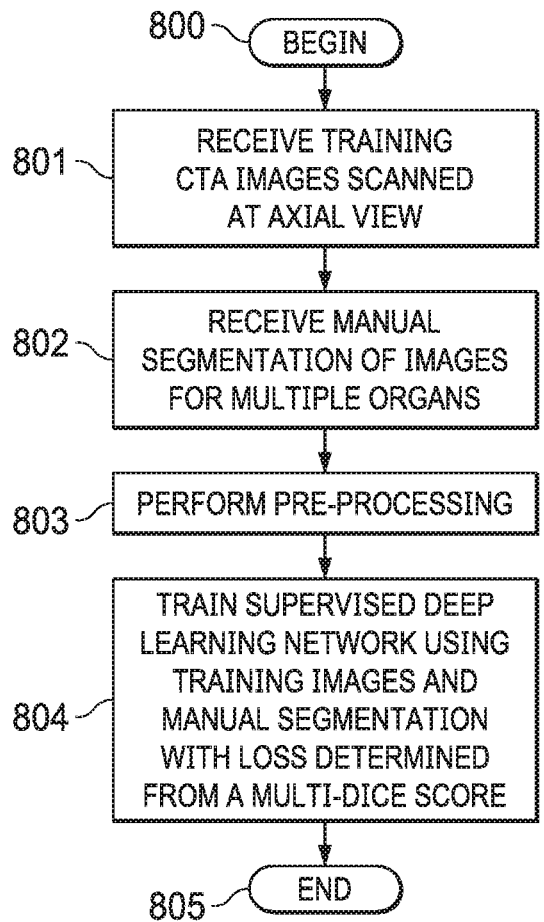
FIG. 8 is a flowchart illustrating operation of mechanism for training a supervised deep learning network for segmentation of anatomical structures in cardiac CTA in accordance with an illustrative embodiment.

FIG. 8 is a flowchart illustrating operation of mechanism for training a supervised deep learning network for segmentation of anatomical structures in cardiac CTA in accordance with an illustrative embodiment. Operation begins (block 800), and the mechanism receives a set of training CTA images (block 801) and receives manual segmentation of images for multiple organs (block 802). The mechanism performs pre-processing (block 803). Pre-processing may encompass down-sampling images in the training CTA volumes.

The mechanism performs trains a supervised deep learning network using the training images and manual segmentation with loss determined from a multi-dice score (block 804). In accordance with the illustrative embodiment, the mechanism trains a supervised deep learning network that is extended to a multi-label network to consider a segmentation problem where the goal is to find segmentation mask images for multiple anatomical structures. The neural network is trained to identify multiple anatomical structures, such as organs, simultaneously. The mechanism trains the supervised deep learning segmentation network by using images and manual segmentation, wherein the loss is determined from a multi-dice score that is a summation of the dice scores for the multiple anatomical structures. Thereafter, operation ends (block 805).

Figure 9:
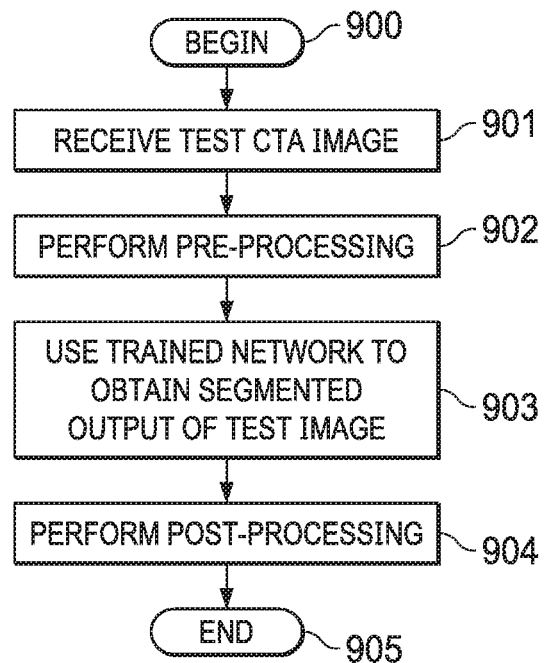
FIG. 9 is a flowchart illustrating operation of a mechanism for testing a trained network for segmentation of anatomical structures in cardiac CTA in accordance with an illustrative embodiment.

FIG. 9 is a flowchart illustrating operation of a mechanism for testing a trained network for segmentation of anatomical structures in cardiac CTA in accordance with an illustrative embodiment. Operation begins (block 900), and the mechanism receives a test CTA image (block 901). The mechanism performs pre-processing (block 902). Pre-processing may encompass down-sampling images in the training CTA volumes.

The mechanism uses the trained supervised deep learning network to obtain a segmented output of the test image (block 903). In accordance with the illustrative embodiment, the supervised deep learning network is trained to consider a segmentation problem where the goal is to find segmentation mask images for multiple anatomical structures. The neural network is trained to identify multiple anatomical structures, such as organs, simultaneously.

Then, the mechanism performs post-processing on the results of performing the V-Net multi-label segmentation (block 904). Post-processing may encompass smoothing on the images resulting from the segmentation operation. Thereafter, operation ends (block 905).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a system for segmentation of anatomical structures in cardiac computed tomography angiography (CTA) using fully convolutional neural networks, the method comprising:
    (a) collecting (i) a set of chest CTA images scanned in the axial view and (ii) a manual segmentation of the images, for each one of multiple anatomical structures, wherein the multiple anatomical structures include ascending/descending/arch/root aorta, left/right/trunk pulmonary artery, vertebrae, left/right atrium, left/right ventricle, left ventricular myocardium, and superior/inferior vena cava;
    (b) pre-processing the images such that they share the same field of view (FOV);
    (c) using both the images and their manual segmentation to train a supervised deep learning segmentation network, wherein loss is determined from a multi-dice score that is a summation of dice scores for all the multiple anatomical structures, each dice score being computed as the similarity between the manual segmentation and the output of the network for one of the anatomical structures;
    (d) testing a given pre-processed image on the trained network, thereby obtaining segmented output of the given image, wherein the segmented output of the given image is segmented for the multiple anatomical structures; and
    (e) performing post-processing on the segmented output of the given image.

2. The method of claim 1, wherein pre-processing the images comprises down-sampling the segmented output of the given image.

3. The method of claim 2, wherein performing post-processing comprises performing up-sampling on the segmented output of the given image.

4. The method of claim 2, wherein performing post-processing comprises performing smoothing on the segmented output of the given image.

5. The method of claim 1, wherein pre-processing the images comprises intensity equalizing the images to eliminate intensity variation between patients.

6. A method in a data processing system comprising a processor and a memory, the memory comprising instructions that are executed by the processor to specifically configure the processor to implement a system for segmentation of anatomical structures in cardiac computed tomography angiography (CTA) using fully convolutional neural networks, the method comprising:
    (a) collecting (i) a set of chest CTA images scanned in the axial view and (ii) a manual segmentation of the images, for each one of multiple anatomical structures;
    (b) pre-processing the images such that they share the same field of view (FOV);
    (c) using both the images and their manual segmentation to train a supervised deep learning segmentation network, wherein loss is determined from a multi-dice score that is a summation of dice scores for all the multiple anatomical structures, each dice score being computed as the similarity between the manual segmentation and the output of the network for one of the anatomical structures, wherein the supervised deep learning segmentation network is extended to a multi-label network, where the goal is to find find segmentation mask image $F_i$, for anatomical structure i, by establishing that $f_j^i \in F_i$, where $f_j^i$ is the $j^{th}$ voxel of the $i^{th}$ segmented foreground, given the ground truth that $g_j^i$ is in the $i^{th}$ ground truth structure, and wherein the overall dice score between the segmentation and the ground truth can be differentiated w.r.t the $i^{th}$ segmentation's $j^{th}$ voxel, yielding the gradient:

$$\frac{\delta D}{\delta f_j^i} = 2\left(\frac{g_j^i\left(\sum_n^N f_n^{i2} + \sum_n^N g_n^{i2}\right) - 2f_j^i \sum_n^N f_n^i g_n^i}{\left(\sum_n^N f_n^{i2} + \sum_n^N g_n^{i2}\right)^2}\right)$$

where N is the total number of voxels in the image;

(d) testing a given pre-processed image on the trained network, thereby obtaining segmented output of the given image, wherein the segmented output of the given image is segmented for the multiple anatomical structures; and (e) performing post-processing on the segmented output of the given image.

7. A computer program product comprising a computer readable storage medium having a computer readable program stored therein, wherein the computer readable program, when executed on a computing device, causes the computing device to implement a system for segmentation of anatomical structures in cardiac computed tomography angiography (CTA) using fully convolutional neural networks, wherein the computer readable program causes the computing device to:

(a) collect (i) a set of chest CTA images scanned in the axial view and (ii) a manual segmentation of the images, for each one of multiple anatomical structures, wherein the multiple anatomical structures include ascending/descending/arch/root aorta, left/right/trunk pulmonary artery, vertebrae, left/right atrium, left/right ventricle, left ventricular myocardium, and superior/inferior vena cava;

(b) pre-process the images such that they share the same field of view (FOV);

(c) use both the images and their manual segmentation to train a supervised deep learning segmentation network, wherein loss is determined from a multi-dice score that is a summation of dice scores for all the multiple anatomical structures, each dice score being computed as the similarity between the manual segmentation and the output of the network for one of the anatomical structures;

(d) test a given pre-processed image on the trained network, thereby obtaining segmented output of the given image, wherein the segmented output of the given image is segmented for the multiple anatomical structures; and (e) perform post-processing on the segmented output of the given image.

8. The computer program product of claim 7, wherein pre-processing the images comprises down-sampling the segmented output of the given image.

9. The computer program product of claim 8, wherein performing post-processing comprises performing up-sampling on the segmented output of the given image.

10. The computer program product of claim 8, wherein performing post-processing comprises performing smoothing on the segmented output of the given image.

11. The computer program product of claim 7, wherein pre-processing the images comprises intensity equalizing the images to eliminate intensity variation between patients.

12. A computer program product comprising a computer readable storage medium having a computer readable program stored therein, wherein the computer readable program, when executed on a computing device, causes the computing device to implement a system for segmentation of anatomical structures in cardiac computed tomography angiography (CTA) using fully convolutional neural networks, wherein the computer readable program causes the computing device to:

(a) collect (i) a set of chest CTA images scanned in the axial view and (ii) a manual segmentation of the images, for each one of multiple anatomical structures;

(b) pre-process the images such that they share the same field of view (FOV);

(c) use both the images and their manual segmentation to train a supervised deep learning segmentation network, wherein loss is determined from a multi-dice score that is a summation of dice scores for all the multiple anatomical structures, each dice score being computed as the similarity between the manual segmentation and the output of the network for one of the anatomical structures, wherein the supervised deep learning segmentation network is extended to a multi-label network, where the goal is to find segmentation mask image $F_i$, for anatomical structure i, by establishing that $f_j^i \in F_i$, where $f_j^i$ is the $j^{th}$ voxel of the $i^{th}$ segmented foreground, given the ground truth that $g_j^i$ is in the $i^{th}$ ground truth structure, and wherein the overall dice score between the segmentation and the ground truth can be differentiated w.r.t the $i^{th}$ segmentation's $j^{th}$ voxel, yielding the gradient:

$$\frac{\delta D}{\delta f_j^i} = 2\left(\frac{g_j^i\left(\sum_n^N f_n^{i2} + \sum_n^N g_n^{i2}\right) - 2f_j^i \sum_n^N f_n^i g_n^i}{\left(\sum_n^N f_n^{i2} + \sum_n^N g_n^{i2}\right)^2}\right)$$

where N is the total number of voxels in the image;

(d) test a given pre-processed image on the trained network, thereby obtaining segmented output of the given image, wherein the segmented output of the given image is segmented for the multiple anatomical structures; and (e) perform post-processing on the segmented output of the given image.

13. An apparatus comprising:

at least one processor; and a memory coupled to the at least one processor, wherein the memory comprises instructions which, when executed by the at least one processor, cause the at least one processor to implement a system for segmentation of anatomical structures in cardiac computed tomography angiography (CTA) using fully convolutional neural networks, wherein the instructions cause the at least one processor to:

(a) collect (i) a set of chest CTA images scanned in the axial view and (ii) a manual segmentation of the images, for each one of multiple anatomical structures, wherein the multiple anatomical structures include ascending/descending/arch/root aorta, left/right/trunk pulmonary artery, vertebrae, left/right atrium, left/right ventricle, left ventricular myocardium, and superior/inferior vena cava;

(b) pre-process the images such that they share the same field of view (FOV);

(c) use both the images and their manual segmentation to train a supervised deep learning segmentation network, wherein loss is determined from a multi-dice score that is a summation of dice scores for all the multiple anatomical structures, each dice score being computed as the similarity between the manual segmentation and the output of the network for one of the anatomical structures;

(d) test a given pre-processed image on the trained network, thereby obtaining segmented output of the given image, wherein the segmented output of the given image is segmented for the multiple anatomical structures; and (e) perform post-processing on the segmented output of the given image.

14. The apparatus of claim 13, wherein pre-processing the images comprises down-sampling the segmented output of the given image and wherein performing post-processing comprises performing up-sampling on the segmented output of the given image.

15. The apparatus of claim 14, wherein performing post-processing comprises performing smoothing on the segmented output of the given image.

16. The apparatus of claim 13, wherein pre-processing the images comprises intensity equalizing the images to eliminate intensity variation between patients.

17. An apparatus comprising:
at least one processor; and
a memory coupled to the at least one processor, wherein the memory comprises instructions which, when executed by the at least one processor, cause the at least one processor to implement a system for segmentation of anatomical structures in cardiac computed tomography angiography (CTA) using fully convolutional neural networks, wherein the instructions cause the at least one processor to:

(a) collect (i) a set of chest CTA images scanned in the axial view and (ii) a manual segmentation of the images, for each one of multiple anatomical structures;

(b) pre-process the images such that they share the same field of view (FOV);

(c) use both the images and their manual segmentation to train a supervised deep learning segmentation network, wherein loss is determined from a multi-dice score that is a summation of dice scores for all the multiple anatomical structures, each dice score being computed as the similarity between the manual segmentation and the output of the network for one of the anatomical structures, wherein the supervised deep learning segmentation network is extended to a multi-label network, where the goal is to find find segmentation mask image $F_i$, for anatomical structure i, by establishing that $f_j^i \in F_i$, where $f_j^i$ is the $j^{th}$ voxel of the $i^{th}$ segmented foreground, given the ground truth that $g_j^i$ is in the $i^{th}$ ground truth structure, and wherein the overall dice score between the segmentation and the ground truth can be differentiated w.r.t the $i^{th}$ segmentation's $j^{th}$ voxel, yielding the gradient:

$$\frac{\delta D}{\delta f_j^i} = 2 \left( \frac{g_j^i \left( \sum_n^N f_n^{i2} + \sum_n^N g_n^{i2} \right) - 2 f_j^i \sum_n^N f_n^i g_n^i}{\left( \sum_n^N f_n^{i2} + \sum_n^N g_n^{i2} \right)^2} \right)$$

where N is the total number of voxels in the image;

(d) test a given pre-processed image on the trained network, thereby obtaining segmented output of the given image, wherein the segmented output of the given image is segmented for the multiple anatomical structures; and (e) perform post-processing on the segmented output of the given image.

* * * * *